(12) United States Patent
Kitamura

(10) Patent No.: US 11,737,809 B2
(45) Date of Patent: Aug. 29, 2023

(54) SURGICAL INSTRUMENT

(71) Applicant: Olympus Corporation, Hachioji (JP)

(72) Inventor: Ojiro Kitamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 924 days.

(21) Appl. No.: 16/717,412

(22) Filed: Dec. 17, 2019

(65) Prior Publication Data

US 2020/0121377 A1   Apr. 23, 2020

Related U.S. Application Data

(63) Continuation of application No. PCT/JP2017/023595, filed on Jun. 27, 2017.

(51) Int. Cl.
*A61B 18/14* (2006.01)
*A61B 18/08* (2006.01)
(Continued)

(52) U.S. Cl.
CPC ........ *A61B 18/085* (2013.01); *A61B 18/1445* (2013.01); *A61B 2018/0063* (2013.01);
(Continued)

(58) Field of Classification Search
CPC .............. A61B 18/085; A61B 18/1445; A61B 2018/00994
See application file for complete search history.

(56) References Cited

U.S. PATENT DOCUMENTS

2006/0259054 A1   11/2006   Masuda et al.
2011/0288579 A1   11/2011   Hyodo
(Continued)

FOREIGN PATENT DOCUMENTS

JP   2004-129871 A   4/2004
JP   2011-239922 A   12/2011
(Continued)

OTHER PUBLICATIONS

Sep. 19, 2017 International Search Report issued in International Patent Application No. PCT/JP2017/023595.
(Continued)

*Primary Examiner* — Linda C Dvorak
*Assistant Examiner* — Ryan T Clark
(74) *Attorney, Agent, or Firm* — Oliff PLC

(57) ABSTRACT

The disclosed technology is directed to a surgical instrument comprises a sheath having respective opposed proximal and distal ends. A pair of grasps is disposed on the distal-end portion of the sheath gripping a treatment target therebetween. A drive shaft is coupled to at least one of the pair of grasps to open or to close the pair of grasps by being moved along the longitudinal axis with respect to the sheath. Electric elements are used to apply treatment energy to the treatment target. A first operating device supplies the electric energy to the electric elements in a first supply state. A first member produces a force to open or close the pair of grasps and applies the force to the drive shaft. A second member is disposed in line with the first member and applies a force to the drive shaft in response to the operation input.

20 Claims, 5 Drawing Sheets

(51) Int. Cl.
*A61B 18/00* (2006.01)
*A61B 18/12* (2006.01)

(52) U.S. Cl.
CPC ............... *A61B 2018/00345* (2013.01); *A61B 2018/00589* (2013.01); *A61B 2018/00601* (2013.01); *A61B 2018/00994* (2013.01); *A61B 2018/126* (2013.01); *A61B 2018/1226* (2013.01); *A61B 2018/1266* (2013.01)

(56) References Cited

U.S. PATENT DOCUMENTS

| | | | |
|---|---|---|---|
| 2012/0022526 A1* | 1/2012 | Aldridge | A61B 18/1445 606/45 |
| 2012/0130420 A1 | 5/2012 | Nicholas et al. | |
| 2013/0289616 A1 | 10/2013 | Suzuki et al. | |
| 2014/0135762 A1* | 5/2014 | Masuda | A61B 18/1445 606/51 |
| 2014/0160015 A1 | 6/2014 | Ogawa et al. | |
| 2015/0335347 A1 | 11/2015 | Hirai et al. | |
| 2018/0036065 A1* | 2/2018 | Yates | A61B 17/320092 |

FOREIGN PATENT DOCUMENTS

| | | |
|---|---|---|
| JP | 2012-110675 A | 6/2012 |
| JP | 2013-035117 A | 2/2013 |
| JP | 2013-042921 A | 3/2013 |
| WO | 2005/122918 A1 | 12/2005 |
| WO | 2013/136587 A1 | 9/2013 |
| WO | 2013/141217 A1 | 9/2013 |

OTHER PUBLICATIONS

Dec. 31, 2019 International Preliminary Report on Patentability issued in International Patent Application No. PCT/JP2017/023595.

* cited by examiner

SURGICAL INSTRUMENT

CROSS-REFERENCE TO RELATED APPLICATION

This application is a continuation application of PCT Application No. PCT/JP2017/023595 filed on Jun. 27, 2017, which is hereby incorporated by reference in its entirety.

TECHNICAL FIELD

The disclosed technology relates to a surgical instrument for gripping a treatment target such as a biological tissue between a pair of grasps.

DESCRIPTION OF THE RELATED ART

US Published Application US2015/0335347A1 discloses a surgical instrument that grips a treatment target such as a biological tissue or biotissue between a pair of grasps and applies treatment energy to the gripped treatment target to treat the same. This surgical instrument applies treatment energy to the gripped treatment target in different states for a treatment that seals the gripped treatment target and a treatment that incises the gripped treatment target. The states in which treatment energy is applied to the treatment target are switched over according to an operation input entered in an operating device.

In a case where treatments are to be made with the surgical instrument disclosed in US2015/0335347A1 or the like, a sealing treatment and an incising treatment require different appropriate magnitudes of gripping forces to be applied to the treatment target because treatment energy is applied in different states for the sealing treatment and the incising treatment. Consequently, it is preferable to switch between gripping forces to be applied to the treatment target depending on a treatment to be performed.

There is a need for a surgical instrument that is capable of switching between gripping forces with which to grip a treatment target, depending on a treatment to be performed.

BRIEF SUMMARY OF EMBODIMENTS

The disclosed technology is directed to a surgical instrument comprises a sheath having respective opposed proximal and distal ends extending along a longitudinal axis. A pair of grasps is disposed on the distal-end portion of the sheath gripping a treatment target therebetween. A drive shaft is configured to be coupled to at least one of the pair of grasps to open or to close the pair of grasps with respect to one another by being moved along the longitudinal axis with respect to the sheath. Electric elements are used to apply treatment energy to the treatment target using electric energy. A first operating device supplies the electric energy to the electric elements in a first supply state in response to an operation input entered therein. A first member produces a force to open or close the pair of grasps with respect to one another and applies the force to the drive shaft. A second member is disposed in line with the first member along the longitudinal axis. The second member applies a force to the drive shaft in response to the operation input entered in the first operating device.

Another aspect of the disclosed technology is directed to a treatment tool comprises a housing having respective first and second ends. A sheath is configured to be attached to the first end of the housing. The sheath having respective opposed proximal and distal ends extending along a longitudinal axis. An effector is mounted to the sheath. The end effector includes a pair of grasps disposed on the distal-end portion of the sheath gripping a treatment target therebetween. A power supply device is attached to the second of the housing via a cable. A drive shaft is configured to be coupled to at least one of the pair of grasps to open or to close the pair of grasps with respect to one another by being moved along the longitudinal axis with respect to the sheath. Electric elements is used to apply treatment energy to the treatment target using electric energy. A first operating device supplies the electric energy to the electric elements in a first supply state in response to an operation input entered therein. A first member produces a force to open or close the pair of grasps with respect to one another and applies the force to the drive shaft. A second member is disposed in line with the first member along the longitudinal axis. The second member applies a force to the drive shaft in response to the operation input entered in the first operating device. The treatment tool is a surgical instrument and the treatment target is a biological tissue.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

First Embodiment

Figure 1:
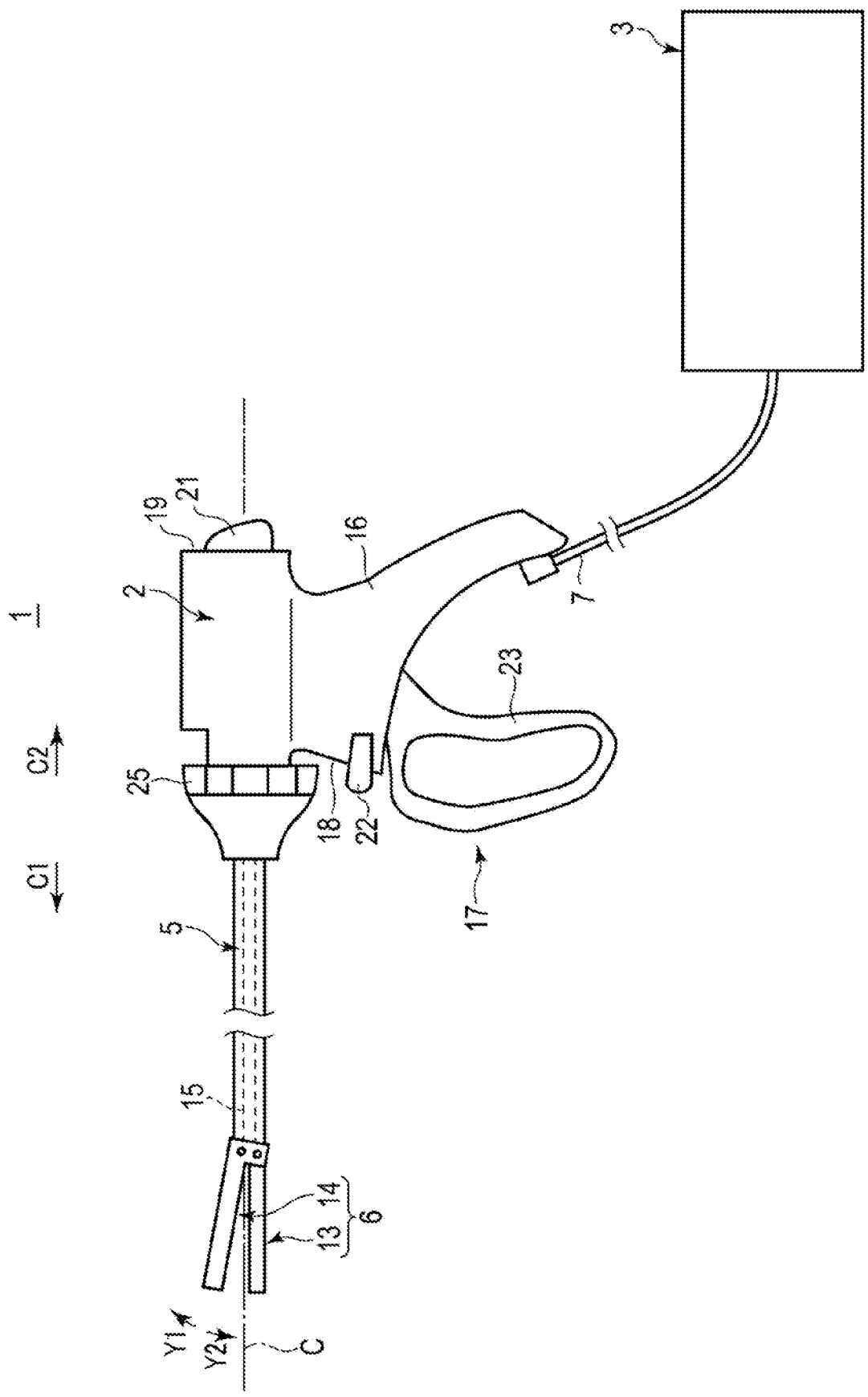
FIG. 1 is a schematic view of a system incorporating a surgical instrument according to a first embodiment.

A first embodiment of the disclosed technology will be described hereinafter with reference to FIGS. 1 through 4C. FIG. 1 is a schematic view of a system incorporating a treatment tool 1 as a surgical instrument according to the present embodiment. The treatment tool 1 is an energy treatment tool sealing and/or incising a biotissue such as a blood vessel, using treatment energy. As illustrated in FIG. 1, the treatment tool 1 includes a housing 2 that can be held, a shaft 5, or a sheath, coupled to a distal-end side of the housing 2, and an end effector 6 mounted on a distal-end portion of the shaft 5. A cable 7 has an end connected to the housing 2. The other end of the cable 7 is separably connected to a power supply device 3. The shaft 5 extends along a longitudinal axis C as a central axis. Here, directions along the longitudinal axis C are referred to as longitudinal directions. A side pointed by one of the longitudinal directions is referred to as a distal-end side, i.e., an arrow C1 side. A side pointed by the other longitudinal direction is referred to as a proximal-end side, i.e., an arrow C2 side.

The housing 2 includes a grip 16, or a fixed handle. A handle 17, or a movable handle, is angularly movably mounted on the housing 2. The handle 17 has a portion disposed in and coupled to the housing 2. The handle 17 also has a portion projecting from the housing 2 and including a catcher 23 that is caught by a surgeon. When the handle 17 is moved angularly with respect to the housing 2, the handle 17 is open away from or closed toward the grip 16.

The end effector 6 includes a first grasp 13 and a second grasp 14 that can be opened away from and closed toward the first grasp 13. The second grasp 14 is angularly movably mounted on the distal-end portion of the shaft 5 about a pivot axis. The handle 17 and the second grasp 14 are coupled to each other by a drive shaft 15 extending in the longitudinal directions in the shaft 5. When the handle 17 is opened away from or closed toward the grip 16, the drive shaft 15 moves in the longitudinal directions with respect to the shaft 5 and the housing 2, opening or closing the space between the pair of grasps 13 and 14 with respect to each other. In another embodiment, both of the grasps 13 and 14 are angularly movably mounted on the shaft 5.

The end effector 6 is opened and closed in directions transverse to, i.e., substantially perpendicular to, the longitudinal axis C. Of the directions in which the end effector 6 is opened and closed, the direction in which the second grasp 14 is opened away from the first grasp 13 is referred to as an opening direction, indicated by an arrow Y1, of the second grasp 14, and the direction in which the second grasp 14 is closed toward the first grasp 13 is referred to as a closing direction, indicated by an arrow Y2, of the second grasp 14. In addition, directions transverse to, i.e., substantially perpendicular to, the longitudinal axis C and also transverse to, i.e., substantially perpendicular to, the directions in which the end effector 6 is opened and closed are referred to as widthwise directions.

A rotary operating knob 25 is mounted on the housing 2. The rotary operating knob 25 is rotatable with respect to the housing 2 about the longitudinal axis C. The rotary operating knob 25 is coupled to the shaft 5. When the rotary operating knob 25 is rotated with respect to the housing 2 about the longitudinal axis C, the rotary operating knob 25, the shaft 5, and the end effector 6 are rotated together with respect to the housing 2. In addition, the drive shaft 15 is rotated in union with the rotary operating knob 25 and the shaft 5 with respect to the housing 2 about the longitudinal axis C.

Operating buttons 21 and 22 are mounted on the housing 2. The operating buttons 21 and 22 function as operation input members in which operation inputs for supplying electric energy from the power supply device 3 to the treatment tool 1 are entered.

Figure 2:
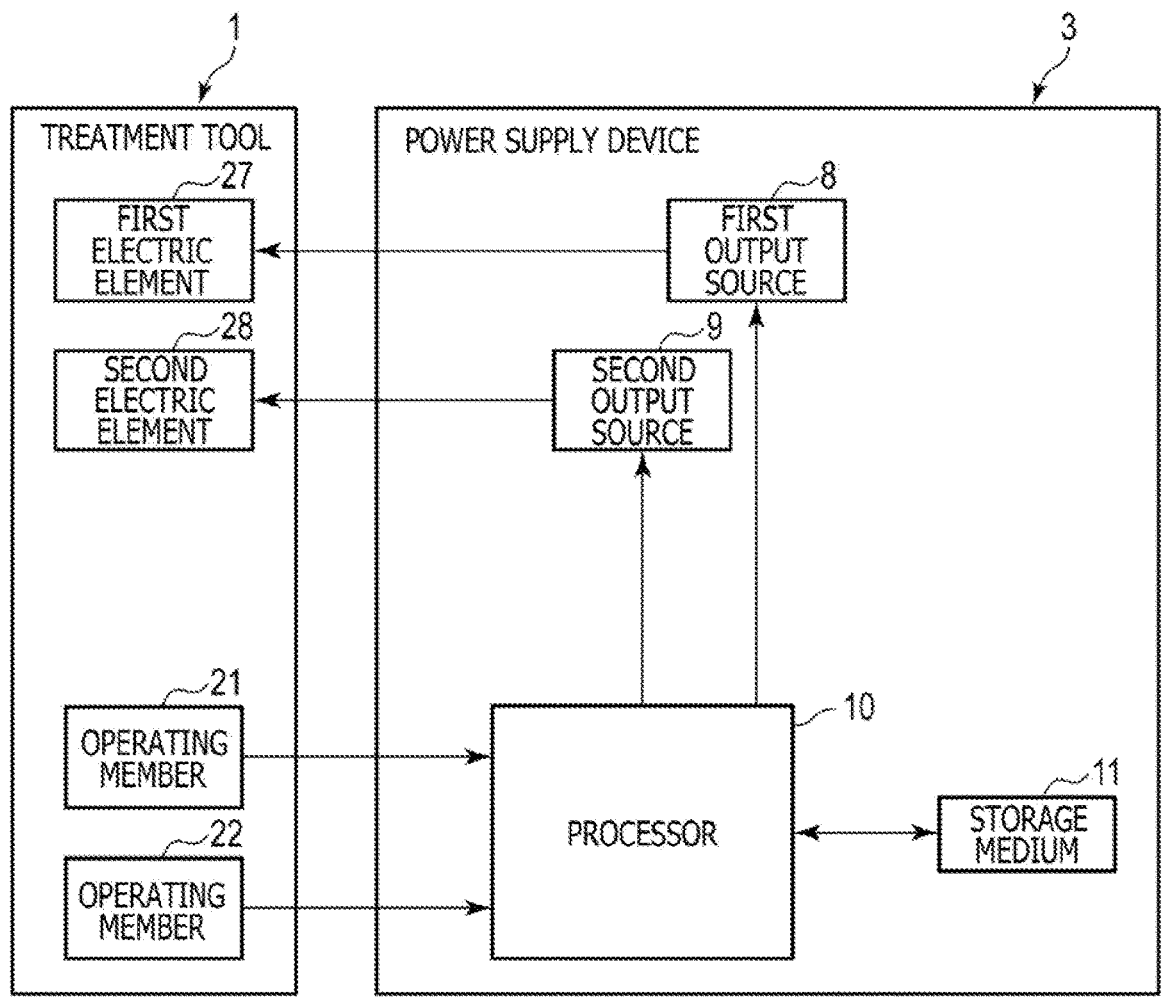
FIG. 2 is a schematic block diagram of an arrangement supplying electric energy to a treatment tool according to the first embodiment.

FIG. 2 is a schematic block diagram of an arrangement supplying electric energy to the treatment tool 1. As illustrated in FIG. 2, the power supply device 3 includes a processor 10 and a storage medium 11. The processor 10 is constructed as an integrated circuit or the like that includes a CPU (Central Processing Unit), an ASIC (Application Specific Integrated Circuit), an FPGA (Field Programmable Gate Array), or the like. The power supply device 3 may include a single processor 10 or a plurality of processors 10. The processor 10 performs processing sequences according to programs stored in the processor 10 or the storage medium 11. The storage medium 11 stores processing programs that are used by the processor 10. The storage medium 11 also stores parameters, functions, tables, and the like that are used in arithmetic operations carried out by the processor 10. The processor 10 detects operation inputs entered in the operating buttons 21, 22.

The treatment tool 1 includes at least one electric element, or an electric device. In the present embodiment, the treatment tool 1 includes a first electric element 27 and a second electric element 28. Further, the power supply device 3 includes a first output source 8 and a second output source 9. The first output source 8 includes a converting circuit or the like, and converts electric power from a battery power supply, an outlet power supply, or the like into electric energy to be supplied to the first electric element 27. Then, the first output source 8 outputs the converted electric energy to the first electric element 27. The second output source 9 includes a converting circuit or the like, and converts electric power from the battery power supply, the outlet power supply, or the like into electric energy to be supplied to the second electric element 28. Further, the second output source 9 outputs the converted electric energy to the second electric element 28. Each of the electric elements 27, 28 is energized when supplied with electric energy.

In the present embodiment, the end effector 6 includes bipolar electrodes as the first electric element 27. The first output source 8 outputs to the bipolar electrodes high-frequency electric power as the electric energy. When the high-frequency electric power is supplied to the bipolar electrodes while a treatment target is being gripped between the grasps 13 and 14, a high-frequency electric current flows through the treatment target between the bipolar electrodes. The high-frequency electric current is applied to the treatment target as treatment energy. The treatment target is modified and sealed or incised by heat caused by the high-frequency electric current.

In the present embodiment, the end effector 6 also includes a heater as the second electric element 28. The second output source 9 outputs to the heater DC electric power or AC electric power as the electric energy. When the heater is supplied with the DC electric power or AC electric power, the heater generates heater heat. When the heater heat is generated while the treatment target is being gripped between the grasps 13 and 14, the heater heat is applied to the treatment target as treatment energy. The treatment target is sealed or incised by the heater heat.

In another embodiment, the housing 2 houses therein an ultrasonic transducer as the second electric element 28. The ultrasonic transducer is connected to a rod member, not illustrated, that functions as one of the grasps 13 and 14. The second output source 9 outputs to the ultrasonic transducer AC electric power in a predetermined frequency range as the electric energy. When the ultrasonic transducer is supplied with the AC electric energy, the ultrasonic transducer produces ultrasonic vibrations that are transmitted through the rod member to one of the grasps 13 and 14. When the ultrasonic vibrations are transmitted to one of the grasps 13 and 14 while the treatment target is being gripped between the grasps 13 and 14, the ultrasonic vibrations are applied to the treatment target as treatment energy. The treatment target is now sealed or incised by frictional heat caused by the ultrasonic vibrations.

The operating button 21, or a first operating device, is mounted on a proximal-end face 19 of the housing 2. The operating button 21 is disposed near the longitudinal axis C and projects toward the proximal-end side from the proximal-end face 19 of the housing 2. The operating button 21 is movable in the longitudinal directions with respect to the housing 2. When the operating button 21 is pushed into the housing 2 and moved toward the distal-end side with respect to the housing 2, an operation input, i.e., a first operation input, is entered in the operating button 21. The housing 2 houses therein two electric contacts, not illustrated, each electrically connected to the processor 10 through an electric path, not illustrated, extending through the housing 2 and the cable 7. When the operating button 21 is pressed, an electric conduction is established between the two electric contacts, transmitting to the processor 10 an electric signal indicating that the operation input is entered in the operating button 21. In an embodiment, in a case where a pressure equal to or larger than a predetermined value is applied to the operating button 21, an electric signal indicating that the operation input is entered in the operating button 21 is transmitted to the processor 10. In addition, in another embodiment, in a case where the operating button 21 has moved a predetermined distance or larger with respect to the housing 2, an electric signal indicating that the operation input is entered in the operating button 21 is transmitted to the processor 10.

The operating button 22, or a second operating device, is mounted on a distal-end face 18 of the housing 2. The operating button 22 is disposed at a position spaced from the longitudinal axis C. The operating button 22 projects toward the distal-end side from the distal-end face 18 of the housing 2. In addition, the operating button 22 is movable in the longitudinal directions with respect to the housing 2. When the operating button 22 is pushed into the housing 2 and moved toward the proximal-end side with respect to the housing 2, an operation input, i.e., a second operation input, is entered in the operating button 22. The housing 2 houses therein two electric contacts, not illustrated, each electrically connected to the processor 10 through an electric path, not illustrated, extending through the housing 2 and the cable 7. When the operating button 22 is pressed, an electric conduction is established between the two electric contacts, transmitting to the processor 10 an electric signal indicating that the operation input is entered in the operating button 22.

The processor 10 controls, based on operations on the operating buttons 21 and 22, the output of the electric energy from each of the output sources 8 and 9 to control the supply of the electric energy to each of the electric elements 27 and 28. In this manner, application of treatment energy such as the high-frequency electric current, the ultrasonic vibrations, and the heater heat to the treatment target is controlled. At least one kind of treatment energy such as the high-frequency electric current, the ultrasonic vibrations, or the heater heat is thus applied to the treatment target.

In a case where an operation input is entered in the operating button 21, the processor 10 supplies electric energy to the treatment tool 1 in a first supply state. In a case where an operation input is entered in the operating button 22, the processor 10 supplies electric energy to the treatment tool 1 in a second supply state that is different from the first supply state.

In the present embodiment, bipolar electrodes are included as the first electric element 27 and a heater is included as the second electric element 28. In the first supply state, electric energy is supplied only to the bipolar electrodes. Therefore, while the treatment target is being gripped between the grasps 13 and 14, as electric energy is supplied to the treatment tool 1 in the first supply state, only high-frequency electric current is applied to the treatment target. In this manner, a treatment is performed to seal or coagulate the treatment target. In the second supply state, electric energy is supplied to both the bipolar electrodes and the heater. Therefore, while the treatment target is being gripped between the grasps 13 and 14, as electric energy is supplied to the treatment tool 1 in the second supply state, both the high-frequency electric current and the heater heat are simultaneously applied to the treatment target. In this manner, a treatment is performed to seal or coagulate the treatment target and at the same time to incise the treatment target.

In the embodiment in which bipolar electrodes are included as the first electric element 27 and an ultrasonic transducer is included as the second electric element 28, for example, in the first supply state, electric energy is supplied to both the bipolar electrodes and the ultrasonic transducer. Consequently, while a treatment target is being gripped between the grasps 13 and 14, as electric energy is supplied to the treatment tool 1 in the first supply state, both high-frequency electric current and ultrasonic vibrations are simultaneously applied to the treatment target. In this manner, a treatment is performed to seal or coagulate the treatment target and at the same time to incise the treatment target. In this embodiment, furthermore, in the second supply state, electric energy is supplied only to the bipolar electrodes. Therefore, while the treatment target is being gripped between the grasps 13 and 14, as electric energy is supplied to the treatment tool 1 in the second supply state, only the high-frequency electric current is applied to the treatment target. In this manner, a treatment is performed to seal or coagulate the treatment target.

In an embodiment in which only heaters are included as the electric elements 27, 28, for example, in each of the first supply state and the second supply state, the heaters are supplied with electric energy. While a treatment target is being gripped between the grasps 13 and 14, as electric energy is supplied to the treatment tool 1 in the first supply state, heater heat is applied to the treatment target as treatment energy. A treatment is thus performed to seal or coagulate the treatment target and at the same time to incise the treatment target. While the treatment target is being gripped between the grasps 13 and 14, as electric energy is supplied to the treatment tool 1 in the second supply state, heater heat is applied to the treatment target. At this time, electric energy that is smaller than the heater heat applied to the treatment target in the first supply state is applied to the heater. A treatment is thus performed to seal or coagulate the treatment target.

Figure 3:
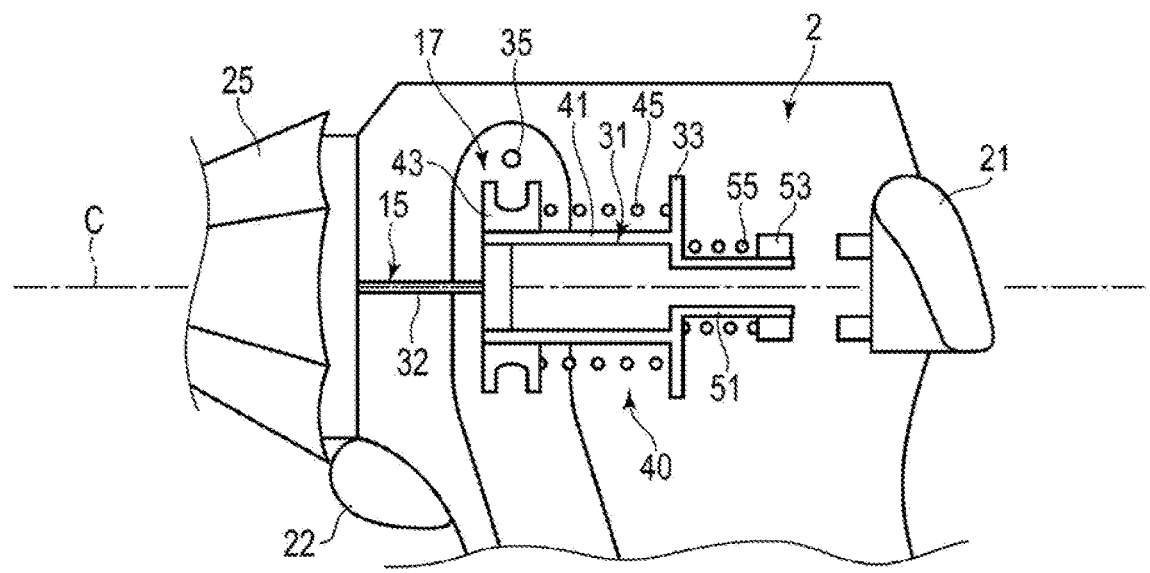
FIG. 3 is a schematic view of an internal structure of a housing according to the first embodiment.

As illustrated in FIG. 3, the handle 17 is coupled to the housing 2 by a support pin 35. The handle 17 moves angularly with respect to the housing 2 about the support pin 35.

The drive shaft 15 includes a movable pipe 31 coupled to the handle 17 in the housing 2 and a movable shaft 32 extending from the movable pipe 31 toward the distal-end side and connected to the end effector 6. The movable pipe 31 is of a substantially tubular shape and extends along the longitudinal axis C. The movable pipe 31 has a central axis that is aligned with or substantially aligned with the central axis, i.e., the longitudinal axis C, of the shaft 5. In other words, the movable pipe 31 and the shaft 5 are disposed coaxially or substantially coaxially with each other. The movable pipe 31 is disposed in the housing 2 such that it is movable along the longitudinal directions with respect to the housing 2 and rotatable with respect to the housing 2 about the longitudinal axis C.

The movable pipe 31 has a protrusion 33 protruding toward an outer circumferential side. The movable pipe 31 has a distal-end portion 41 positioned on a distal-end side of the protrusion 33 and a proximal-end portion 51 positioned on a proximal-end side of the protrusion 33. The protrusion 33 is positioned between the distal-end portion 41 and the proximal-end portion 51.

The housing 2 houses a spring mechanism 40 therein. The spring mechanism 40 includes a spring 45, or a first resilient member, connected to or held in contact with the movable pipe 31, a slider 43 connected to or held in contact with the spring 45, a spring 55, or a second resilient member, disposed in line with and coaxially with the spring 45, and a slider 53 connected to or held in contact with the spring 55.

The slider 43, or a first slider, that is of a tubular shape, is disposed on an outer circumferential surface of the distal-end portion 41 of the movable pipe 31. The slider 43 is spaced from the protrusion 33 toward the distal-end side. The slider 43 is mounted on the movable pipe 31 for movement thereon in the longitudinal directions. The slider 43 is coupled to the handle 17. When the handle 17 is moved angularly with respect to the housing 2, the slider 43 is moved in the longitudinal directions with respect to the housing 2. The slider 43 is coupled to the handle 17 at a position between the support pin 35 and the catcher 23. Therefore, when the catcher 23 of the handle 17 is moved toward the grip 16, i.e., toward the proximal-end side, the slider 43 is moved toward the proximal-end side with respect to the housing 2.

The spring 45 that is resilient is disposed on the outer circumferential surface of the distal-end portion 41 of the movable pipe 31. The spring 45 is in the form of a helical spring. The spring 45 is disposed between the protrusion 33 and the slider 43. The spring 45 extends along the longitudinal axis C, and is disposed coaxially or substantially coaxially with the movable pipe 31. The spring 45 has a distal end connected to or held in contact with the slider 43. The spring 45 has a proximal end connected to or held in contact with the protrusion 33. The spring 45 is disposed between the protrusion 33 and the slider 43 in a reference state in which the spring 45 has been compressed only with a predetermined displacement from a natural state, or a natural length, thereof. The spring 45 has an elastic modulus $k1$. When the handle 17 and the grip 16 are closed with respect to each other, i.e., brought together to close the space therebetween, the spring 45 is displaced, i.e., compressed, by a distance $x1$ from the natural state, or the natural length, thereof. A resilient force $F1=k1 \cdot x1$ from the spring 45 acts on the protrusion 33 toward the proximal-end side.

The slider 53, or a second slider, that is of a tubular shape, is disposed on an outer circumferential surface of the proximal-end portion 51 of the movable pipe 31. The slider 53 is spaced from the protrusion 33 toward the proximal-end side. The slider 53 is mounted on the movable pipe 31 for movement thereon in the longitudinal directions. Electric contacts are mounted on the slider 53 and have an electric contact state that is variable depending on a pressed state of the operating button 21.

The spring 55 that is resilient is disposed on the outer circumferential surface of the proximal-end portion 51 of the movable pipe 31. The spring 55 is in the form of a helical spring. The spring 55 is disposed between the protrusion 33 and the slider 53. The spring 55 extends along the longitudinal axis C, and is disposed coaxially or substantially coaxially with the movable pipe 31 or the spring 45. The spring 45 and the spring 55 are disposed in line with each other. The spring 55 has a proximal end connected to or held in contact with the slider 53. The spring 55 has a distal end connected to or held in contact with the protrusion 33. While the operating button 21 is not being pressed, the slider 53 has a proximal-end face spaced from the operating button 21. The spring 55 is disposed between the protrusion 33 and the slider 53 in a reference state in which the spring 55 has been compressed only with a predetermined displacement from a natural state, or a natural length, thereof. The spring 55 has an elastic modulus $k2$. The spring 55 is displaced, i.e., compressed, by a distance $x2$ from the natural state, or the natural length, thereof. A resilient force $F2=k2 \cdot x2$ from the spring 55 acts on the protrusion 33 in a direction toward the distal-end side.

The protrusion 33 of the movable pipe 31 is pressed toward the proximal-end side under the resilient force F1 from the spring 45 and pressed toward the distal-end side under the resilient force F2 from the spring 55. Therefore, the resultant of the resilient force F1 and the resilient force F2 acts on the movable pipe 31. Here, the resilient force F2 acts on an opposite side to the resilient force F1 with respect to the longitudinal directions. In addition, the elastic moduli $k1$ and $k2$, the displacements $x1$ and $x2$, and the like are set to such values that the magnitude of the resilient force F2 is smaller than the magnitude of the resilient force F1. Therefore, the resultant that represents the difference calculated by subtracting the resilient force F2 from the resilient force F1 acts on the movable pipe 31 toward the proximal-end side.

When the catcher 23 of the handle 17 is pressed toward the grip 16, the handle 17 is moved angularly about the support pin 35 with respect to the housing 2 about and the catcher 23 of the handle 17 is moved toward the proximal-end side with respect to the housing 2. At this time, the handle 17 transmits a drive force through the slider 43, the spring 45, and the protrusion 33 to the drive shaft 15, causing the slider 43, the spring 45, and the drive shaft 15 to move together toward the proximal-end side with respect to the housing 2. When the drive shaft 15 is moved toward the proximal-end side with respect to the housing 2, i.e., the shaft 5, the end effector 6 is closed, closing the space between the grasps 13 and 14. At this time, the slider 43 is moved in unison with the movable pipe 31 toward the proximal-end side with respect to the housing 2. Consequently, the position of the slider 43 with respect to the movable pipe 31 remains unchanged. The spring 45 thus does not change from the reference state.

Figure 4A:
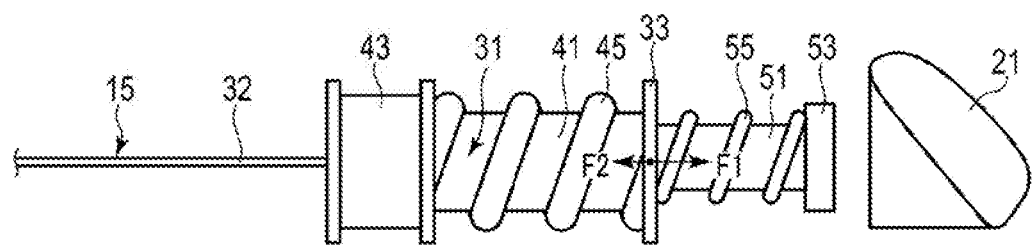
FIG. 4A is a schematic view of the internal structure of the housing in a state in which a treatment target is compressed to a certain extent between a pair of grasps according to the first embodiment and the pair of grasps have stopped being closed.
Figure 4B:
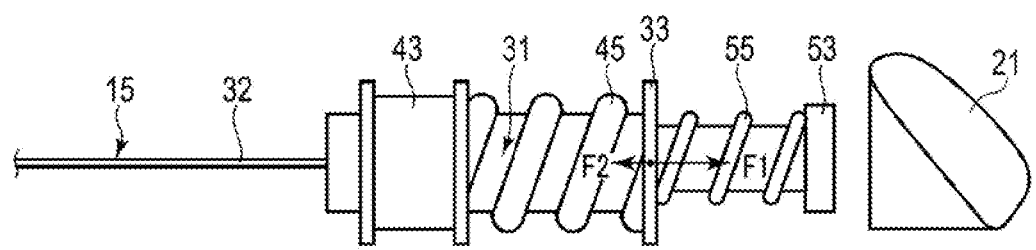
FIG. 4B is a schematic view of the internal structure of the housing at the time a handle is further gripped toward a grip in the state illustrated in FIG. 4A.

When the space between the grasps 13 and 14 is closed, compressing the treatment target to a certain extent, the end effector 6 stops being closed, and the movable pipe 31 stops moving toward the proximal-end side with respect to the housing 2 (see FIG. 4A). Upon further gripping the handle 17 with respect to the grip 16 in the abovementioned state, since the drive shaft 15 has stopped moving with respect to the housing 2, the slider 43 is moved toward the proximal-end side with respect to the movable pipe 31, as illustrated in FIG. 4B. At this time, as the slider 43 is moved toward the proximal-end side with respect to the movable pipe 31, the spring 45 is further compressed from its reference state. Therefore, the resilient force F1 that acts from the spring 45 on the protrusion 33 becomes larger than when the spring 45 is in the reference state. The handle 17 is closed on the grip 16 until the handle 17 abuts against a limiting member on the grip 16 or the like. The protrusion 33 is pressed toward the proximal-end side by the spring 45. The resilient force F1 that acts on the protrusion 33 is determined by the displacement x1 of the spring 45 from its natural length regardless of the magnitude of the force that a surgeon applies to the handle 17.

While the operating button 21 is not being pressed, the proximal-end face of the slider 53 is spaced from the operating button 21. Consequently, the resilient force F2 from the spring 55 in the reference state acts on the protrusion 33.

Figure 4C:
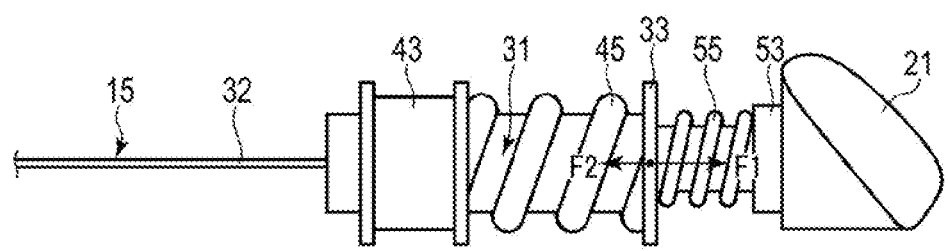
FIG. 4C is a schematic view of the internal structure of the housing at the time an operation input is entered in a first operating device in the state illustrated in FIG. 4B.

When an operation input is entered in the operating button 21 while the space between the handle 17 and the grip 16 is being closed, the operating button 21 is pushed into the housing 2 and hence moved toward the distal-end side with respect to the housing 2. At this time, as illustrated in FIG. 4C, the operating button 21 is pressed against the slider 53 from the proximal-end side in the housing 2, pushing the slider 53 toward the distal-end side. With the handle 17 being gripped with respect to the grip 16, the movable pipe 31 stops being moved with respect to the housing 2. Therefore, the slider 53 is moved toward the distal-end side with respect to the movable pipe 31. As the slider 53 is moved toward the distal-end side with respect to the movable pipe 31, the spring 55 is further compressed from its reference state. Therefore, the resilient force F2 that acts from the spring 55 on the protrusion 33 becomes larger than when the spring 55 is in the reference state. When the operating button 21 is pressed, the resilient force F2 that acts from the spring 55 on the protrusion 33 toward the distal-end side thus becomes larger than when the operating button 21 is not pressed. As the resilient force F2 becomes larger, the resultant acting on the protrusion 33 toward the proximal-end side becomes smaller. As described hereinbefore, the distance x2 by which the spring 55 is compressed changes commensurate with the operation input entered in the operating button 21.

The resultant acting on the movable pipe 31 is transmitted through the movable shaft 32 to the end effector 6, affecting the gripping force that is applied to the treatment target between the grasps 13 and 14. For example, the larger the resultant that acts on the movable pipe 31 toward the proximal-end side is, the larger the gripping force that is applied to the treatment target between the grasps 13 and 14 becomes.

Operation and advantages of the treatment tool 1 according to the present embodiment will be described hereinafter. For performing a treatment using the treatment tool 1, a surgeon inserts the end effector 6 into a body cavity such as an abdominal cavity, and places a biotissue such as a blood vessel as a treatment target between the grasps 13 and 14. Then, the surgeon holds the housing 2 and the catcher 23 of the handle 17, and presses the handle 17 toward the grip 16, closing the grasps 13 and 14 relatively to each other. With the space between the grasps 13 and 14 being closed, the surgeon further grips the handle 17 with respect to the grip 16, closing the handle 17 on the grip 16. At this time, the spring 55 is kept in its reference state, and the spring 45 is further compressed from its reference state. Therefore, the resultant of the resilient force F1 from the spring 45 further compressed from its reference state and the resilient force F2 from the spring 55 kept in its reference state acts on the protrusion 33 of the movable pipe 31.

Then, when an operation input is entered in the operating button 22, electric energy is supplied to the treatment tool 1 in the second supply state. The end effector 6 applies treatment energy to the treatment target, simultaneously sealing or coagulating and incising the treatment target gripped between the grasps 13 and 14. At this time, the compressed state of the spring 45, i.e., the distance by which the spring 45 is compressed, and the compressed state of the spring 55, i.e., the distance by which the spring 55 is compressed, remain unchanged. Therefore, the resultant of the resilient force F1 that acts from the spring 45 on the protrusion 33 and the resilient force F2 that acts from the spring 55 on the protrusion 33 remains unchanged. In the second supply state, the resultant of the resilient force F1 from the spring 45 further compressed from its reference state and the resilient force F2 from the spring 55 kept in its reference state thus acts on the drive shaft 15.

When an operation input is entered in the operating button 21, electric energy is supplied to the treatment tool 1 in the first supply state. The end effector 6 applies treatment energy to the treatment target, sealing or coagulating the treatment target gripped between the grasps 13 and 14. At this time, though the compressed state of the spring 45 remains unchanged, the spring 55 is further compressed from its reference state. Therefore, the resultant of the resilient force F1 from the spring 45 further compressed from its reference state and the resilient force F2 from the spring 55 further compressed from its reference state acts on the protrusion 33 of the movable pipe 31. The resilient force F2 that acts from the spring 55 on the protrusion 33 is larger than in the case where the spring 55 is kept in its reference state. In the first supply state, therefore, the resilient force F2 acting on the movable pipe 31 toward the distal-end side is larger than in the second supply state, and the resultant acting on the movable pipe 31 toward the proximal-end side is smaller. Accordingly, the gripping force applied to the treatment target is smaller in the first supply state than in the second supply state.

In a case where heat generated by a heater is used as treatment energy, it is preferable to apply a large gripping force to a treatment target in a treatment for incising the treatment target. On the other hand, in a treatment for sealing a treatment target, a large gripping force cannot be applied to the treatment target because it might sever the treatment target. According to the present embodiment, in the second supply state for incising the treatment target, a larger gripping force is applied to the treatment target than in the first supply state for sealing the treatment target. Therefore, in an incising treatment, a larger gripping force than in a sealing treatment is applied to the treatment target. The treating performance of the treatment tool 1 is thus increased in treatments using the treatment tool 1. As described hereinbefore, since the gripping force applied to the treatment target is variable depending on a treatment on the treatment target, an appropriate gripping force depending on the treatment can be applied to the treatment target.

Furthermore, according to the present embodiment, the gripping force applied to the treatment target changes as the displacement x2 of the spring 55 coupled to the operating button 21 changes. Therefore, the gripping force is variable while the displacement x1 of the spring 45 is kept constant. In other words, while the handle 17 is being gripped, different gripping forces depending on treatments can be applied to the treatment target.

Moreover, the spring 55 is disposed substantially coaxially with and in line with the spring 45. Consequently, a hypothetical point of action where the resilient force F1 acts on the movable pipe 31 from the spring 45 and a hypothetical point of action where the resilient force F2 acts on the movable pipe 31 from the spring 55 agree essentially with each other. This increases the stability with which to operate the treatment tool 1 for changing the compressed states of the springs 45 and 55. In addition, the transmittability of the resilient forces F1 and F2 as they act on the movable pipe 31 increases.

Furthermore, the springs 45 and 55 are disposed substantially coaxially with the movable pipe 31. Therefore, the transmittability of the resultant of the resilient forces F1 and F2 when it is transmitted through the movable pipe 31 to the end effector 6 increases.

First Modification of the First Embodiment

Figure 5:
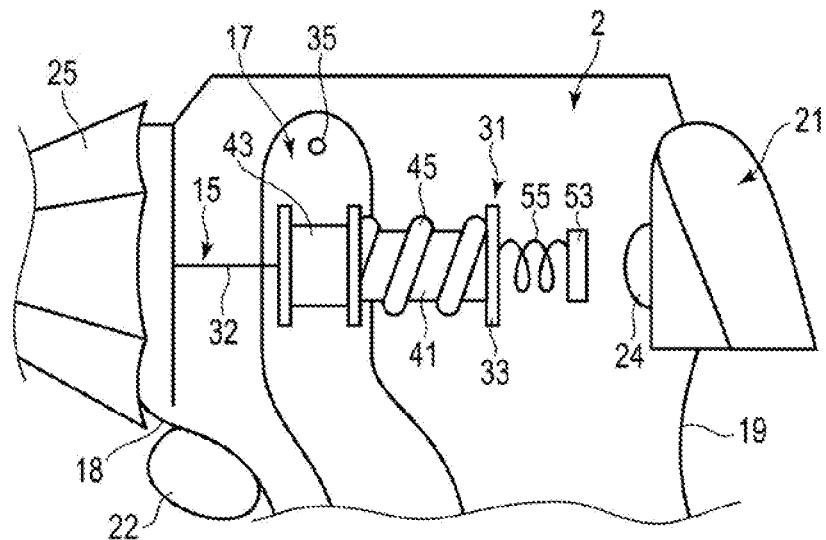
FIG. 5 is a schematic view of an internal structure of a housing according to a first modification of the first embodiment.

A first modification of the present embodiment will be described hereinafter with reference to FIG. 5. According to the present modification, the spring 55 is disposed on the movable pipe 31 in a natural state, or a natural length, thereof. While the grip 16 and the handle 17 are being closed with respect to each other and the operating button 21 is not being pressed, the operating button 21 and the slider 53 are spaced from each other.

A dome switch 24 is mounted on the operating button 21. The dome switch 24 is disposed in confronting relation to the slider 53. The dome switch 24 has a plurality of electric contacts disposed therein. When a pressure equal to or larger than a predetermined value acts on the dome switch 24, the electric contacts thereof contact each other, sending an electric signal indicating that an operation input is entered in the operating button 21 to the processor 10, as described hereinbefore.

While the grip 16 and the handle 17 are being closed respect to each other and the operating button 21 is not being pressed, the dome switch 24 and the slider 53 are spaced from each other. Therefore, the spring 55 is kept in its natural state, with its resilient force F2 being 0. Consequently, only the resilient force F1 from the spring 45 further compressed from its reference state acts on the protrusion 33 of the movable pipe 31. The resultant of the resilient force F1 and the resilient force F2 acting on the protrusion 33 is thus substantially the same as the resilient force F1. When an operation input is entered in the operating button 22, the resultant acting on the protrusion 33 remains unchanged.

When the operating button 21 is pressed, the operating button 21 is moved toward the distal-end side with respect to the housing 2, bringing the dome switch 24 into contact with the slider 53 from the proximal-end side. The slider 53 is pressed toward the distal-end side by the dome switch 24, and the dome switch 24 is pressed toward the proximal-end side by the spring 55. A force equal to or larger than the predetermined value is applied to the dome switch 24, i.e., the distance x2 by which the spring 55 is compressed becomes equal to or larger than a predetermined value, so that electric energy in the first supply state is supplied from the power supply device 3 to the treatment tool 1.

When an operation input is entered in the operating button 21, the slider 53 is moved toward the distal-end side with respect to the movable pipe 31, compressing the spring 55 from its natural state. The resilient force F2 (=k2·x2) from the spring 55 acts on the protrusion 33 toward the distal-end side. The protrusion 33 is pressed toward the distal-end side by the spring 55. Therefore, when an operation input is entered in the operating button 21, the resilient force F2 acting from the spring 55 on the protrusion 33 toward the distal-end side becomes larger than in the case where no operation input is entered in the operating button 21, reducing the resultant acting on the protrusion 33 toward the proximal-end side. According to the present modification, consequently, since the gripping force applied to the treatment target is variable depending on a treatment on the treatment target, a gripping force suitable for the treatment can be applied to the treatment target.

According to the present modification, as the distance x2 by which the spring 55 is compressed becomes equal to or larger than the predetermined value, an electric signal indicating that the operation input is entered in the operating button 21 is transmitted to the power supply device 3, which outputs electric energy in the first supply state. Therefore, a treatment using electric energy is performed after the gripping force applied to the treatment target has changed to a magnitude suitable for the treatment.

Second Modification of the First Embodiment

Figure 6:
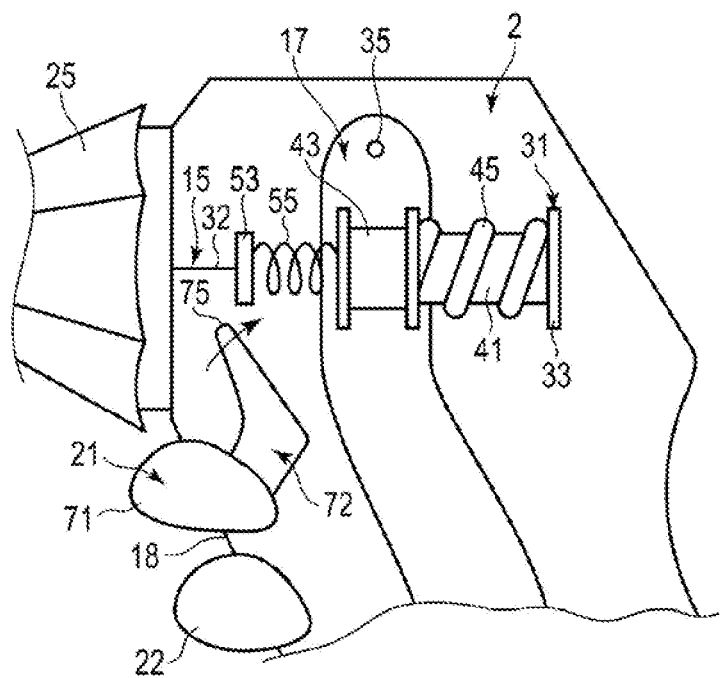
FIG. 6 is a schematic view of an internal structure of a housing according to a second modification of the first embodiment.

A second modification of the present embodiment will be described hereinafter with reference to FIG. 6. According to the present modification, the operating button 21, or the first operating device, is mounted on the distal-end face 18 of the housing 2. The operating button 21 includes an operating member 71 and a link member 72. The operating member 71 is movable along the longitudinal directions with respect to the housing 2. The housing 2 houses two electric contacts, not illustrated, therein, each electrically connected to the power supply device 3 through an electric circuit, not illustrated, extending through the housing 2 and the cable 7. When the operating member 71 is pressed toward the housing 2, electric conduction is established between the two electric contacts, transmitting an electric signal indicating that the operation input is entered in the operating button 21 to the processor 10. Then, electric energy in the first supply state is supplied from the power supply device 3 to the treatment tool 1.

According to the present modification, furthermore, when an operation input is entered in the operating button 21, i.e., in the first supply state, the treatment target is incised. When an operation input is entered in the operating button 22, i.e., in the second supply state, the treatment target is sealed.

The link member 72 is disposed in the housing 2. The link member 72 has an end coupled to the operating member 71. The other end of the link member 72 extends toward the movable pipe 31 and has an abutment portion 75. When the operating member 71 is moved with respect to the housing 2, the abutment portion 75 is moved with respect to the housing 2.

According to the present modification, furthermore, the slider 53 and the spring 55, or the second resilient member, are mounted on the distal-end side of the slider 43. The proximal end of the spring 55 is connected to or held in contact with the slider 43. The distal end of the spring 55 is connected to or held in contact with the slider 53. The spring 55 is disposed between the slider 43 and the slider 53 in a non-urged state, i.e., in a natural state thereof. The spring 55 is disposed in line with and coaxially or substantially coaxially with the spring 45 and the movable pipe 31.

While the handle 17 and the grip 16 are closed with respect to each other and the operating member 71 is not being pressed, the abutment portion 75 of the link member 72 and the slider 53 are spaced from each other. Therefore, the spring 55 is kept in its natural state, with its resilient force F2 being 0. Consequently, only the resilient force F1 from the spring 45 further compressed from its reference state acts on the protrusion 33 of the movable pipe 31. The resultant of the resilient force F1 and the resilient force F2 acting on the protrusion 33 is thus substantially the same as the resilient force F1. When an operation input is entered in the operating button 22, i.e., in the second supply state, the resultant acting on the protrusion 33 remains unchanged.

When the operating member 71 of the operating button 21 is pressed, the operating member 71 is moved toward the proximal-end side with respect to the housing 2, and the abutment portion 75 abuts against the slider 53 from the distal-end side. Pressed toward the proximal-end side by the abutment portion 75, the slider 53 is moved toward the proximal-end side with respect to the movable pipe 31, compressing the spring 55 from its natural state. The resilient force F2 (=k2·x2) from the spring 55 acts on the slider 43 toward the proximal-end side. Therefore, the protrusion 33 is pressed toward the proximal-end side by the spring 55 through the slider 43 and the spring 45.

When an operation input is entered in the operating button 21, i.e., in the first supply state, the protrusion 33 of the movable pipe 31 is pressed toward the proximal-end side under the resilient force F1 from the spring 45 and pressed toward the proximal-end side under the resilient force F2 from the spring 55. Consequently, the resultant of the resilient force F1 from the spring 45 and the resilient force F2 from the spring 55 acts on the movable pipe 31. The resilient force F1 and the resilient force F2 are forces directed toward the same side. The resultant that represents the sum of the resilient force F1 and the resilient force F2 thus acts on the movable pipe 31 toward the proximal-end side. According to the present modification, therefore, when an operation input is entered in the operating button 21, the resultant of the resilient force F1 and the resilient force F2 acting on the protrusion 33 is larger than when an operation input is entered in the operating button 22. Consequently, in the first supply state, i.e., a first output state, the resultant acting on the movable pipe 31 is larger than in the second supply state, i.e., a second output state.

According to the present modification, therefore, in the first supply state for incising the treatment target, a larger gripping force is applied to the treatment target than in the second supply state for sealing the treatment target. Accordingly, since the gripping force applied to the treatment target is variable depending on a treatment on the treatment target, a gripping force suitable for the treatment can be applied to the treatment target.

Second Embodiment

Figure 7:
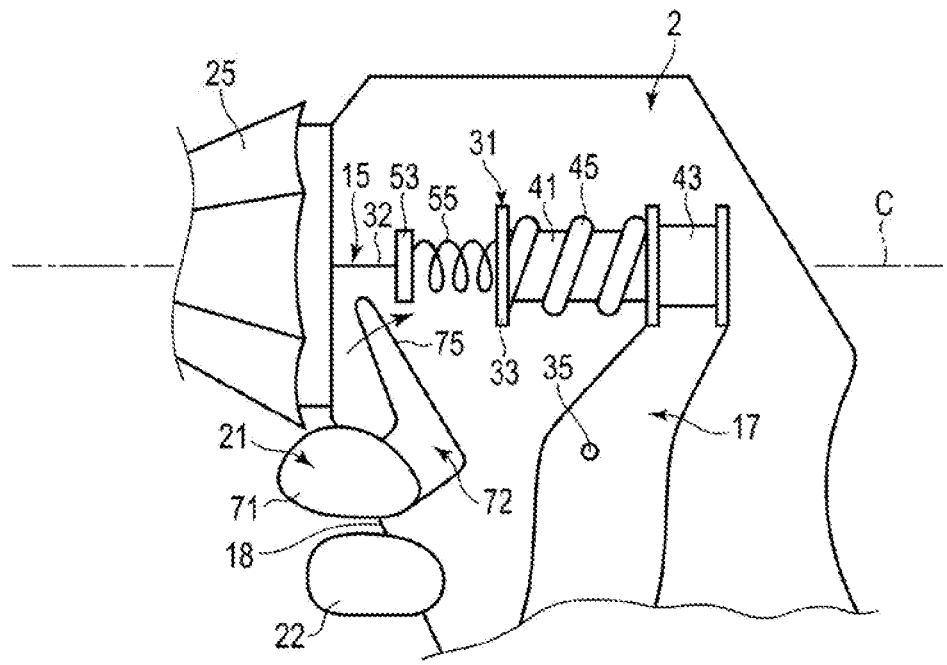
FIG. 7 is a schematic view of an internal structure of a housing according to a second embodiment.

A second embodiment of the disclosed technology will be described hereinafter with reference to FIG. 7. The second embodiment represents a modification, to be described hereinafter, of the structure according to the first embodiment. Those parts of the second embodiment which are identical to those of the first embodiment are denoted by identical numeral reference, and their description will be omitted below.

According to the present embodiment, as with the second modification of the first embodiment, the operating button 21 is mounted on the distal-end face 18 of the housing 2, and includes the operating member 71 and the link member 72.

The slider 43 and the spring 45, or the first resilient member, are mounted on the movable pipe 31 closer to the proximal-end side than the protrusion 33. The slider 53 and the spring 55, or the second resilient member, are mounted on the movable pipe 31 closer to the distal-end side than the protrusion 33. The spring 45 extends along the longitudinal axis C and is disposed coaxially or substantially coaxially with the movable pipe 31. The proximal end of the spring 45 is connected to or held in contact with the slider 43. The distal end of the spring 45 is connected to or held in contact with the protrusion 33 of the movable pipe 31. The spring 45 is disposed between the protrusion 33 and the slider 43 in a reference state in which the spring 45 has been compressed only with a predetermined displacement from a natural state, or a natural length, thereof.

The spring 55 extends along the longitudinal axis C, and is disposed coaxially or substantially coaxially with the movable pipe 31. The distal end of the spring 55 is connected to or held in contact with the slider 53. The proximal end of the spring 55 is connected to or held in contact with the protrusion 33 of the movable pipe 31. The spring 55 is disposed between the protrusion 33 and the slider 53 in a non-urged state, i.e., in a natural state thereof.

The slider 43 is mounted on the handle 17 at a position that is opposite the catcher 23 across the support pin 35. Therefore, when the catcher 23 of the handle 17 is closed on the grip 16, the handle 17 is moved angularly about the support pin 35 with respect to the housing 2, moving the slider 43 toward the distal-end side with respect to the housing 2. As the slider 43 and the drive shaft 15 are moved together toward the distal-end side with respect to the housing 2, the grasps 13 and 14 are closed relatively to each other.

When the grasps 13 and 14 are closed relatively to each other, the end effector 6 stops being closed, and the drive shaft 15 stops moving toward the distal-end side with respect to the housing 2. Upon further gripping the handle 17 with respect to the grip 16 in the abovementioned state, the slider 43 is moved toward the distal-end side with respect to the movable pipe 31. At this time, as the slider 43 is moved toward the distal-end side with respect to the movable pipe 31, the spring 45 is further compressed from its reference state. The handle 17 and the grip 16 are closed with respect to each other. The resilient force F1=k1·x1 from the spring 45 acts on the protrusion 33 toward the distal-end side.

While the handle 17 and the grip 16 are closed with respect to each other and the operating member 71 is not being pressed, the abutment portion 75 of the link member 72 and the slider 53 are spaced from each other. Therefore, the spring 55 is kept in its natural state, with its resilient force F2 being 0. Consequently, only the resilient force F1 from the spring 45 further compressed from its reference state acts on the protrusion 33 of the movable pipe 31. The resultant of the resilient force F1 and the resilient force F2 acting on the protrusion 33 is thus substantially the same as the resilient force F1. When an operation input is entered in the operating button 22, i.e., in the second output state, the resultant acting on the protrusion 33 remains unchanged.

When the operating member 71 of the operating button 21 is pressed, the operating member 71 is moved toward the proximal-end side with respect to the housing 2, and the abutment portion 75 abuts against the slider 53 from the distal-end side. The slider 53 is moved toward the proximal-end side with respect to the movable pipe 31, compressing the spring 55 from its natural state. The resilient force F2 (=k2·x2) from the spring 55 acts on the protrusion 33 toward the proximal-end side. Therefore, the protrusion 33 is pressed toward the proximal-end side by the spring 55.

When an operation input is entered in the operating button 21, i.e., in the first supply state, the protrusion 33 of the movable pipe 31 is pressed toward the distal-end side under the resilient force F1 from the spring 45 and pressed toward the proximal-end side under the resilient force F2 from the spring 55. The magnitude of the resilient force F1 is larger than the magnitude of the resilient force F2. Therefore, the resultant that represents the difference calculated by subtracting the resilient force F2 from the resilient force F1 acts on the movable pipe 31 toward the distal-end side. In the first supply state, the resultant acting on the movable pipe 31 is thus smaller than in the second supply state.

According to the present embodiment, in the second supply state for incising the treatment target, a larger gripping force is applied to the treatment target than in the first supply state for sealing the treatment target. Therefore, since the gripping force applied to the treatment target is variable depending on the selected state in which electric energy is supplied, a gripping force suitable for the treatment can be applied to the treatment target.

First Modification of the Second Embodiment

Figure 8:
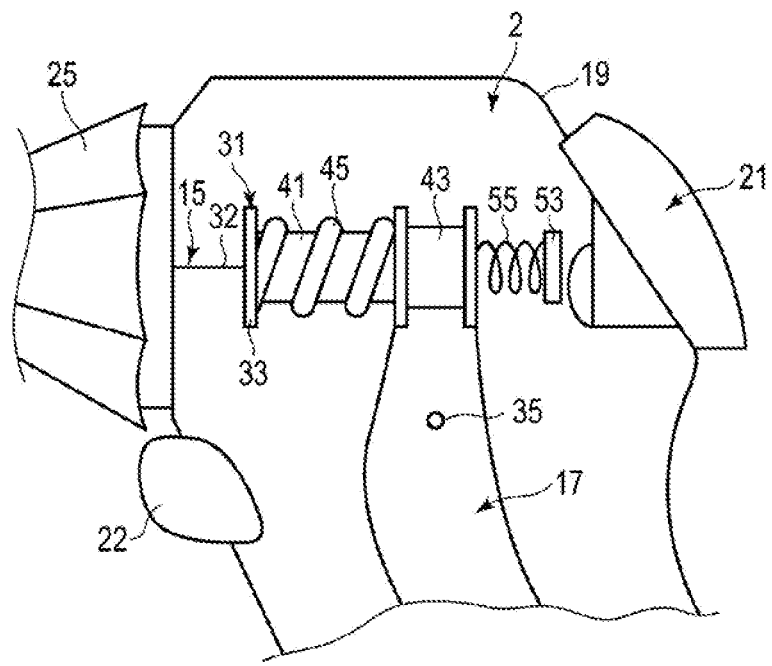
FIG. 8 is a schematic view of an internal structure of a housing according to a first modification of the second embodiment.

A first modification of the present embodiment will be described hereinafter with reference to FIG. 8. According to the present modification, the operating button 21 is mounted on the proximal-end face 19 of the housing 2.

When an operation input is entered in the operating button 21, i.e., in the first supply state, the treatment target is incised. When an operation input is entered in the operating button 22, i.e., in the second supply state, the treatment target is sealed.

The slider 53 and the spring 55, or the second resilient member, 55 are mounted on the movable pipe 31 on the proximal-end side of the slider 43. The distal end of the spring 55 is connected to or held in contact with the slider 43. The proximal end of the spring 55 is connected to or held in contact with the slider 53. The spring 55 is disposed between the slider 43 and the slider 53 in a non-urged state, i.e., in a natural state thereof. The spring 55 is disposed in line with and coaxially or substantially coaxially with the spring 45 and the movable pipe 31.

While the handle 17 and the grip 16 are closed with respect to each other and the operating button 21 is not being pressed, the slider 53 and the operating button 21 are spaced from each other. Therefore, the spring 55 is kept in its natural state, with its resilient force F2 being 0. Consequently, only the resilient force F1 from the spring 45 further compressed from its reference state acts on the protrusion 33 of the movable pipe 31. The resultant of the resilient force F1 and the resilient force F2 acting on the protrusion 33 is thus substantially the same as the resilient force F1. When an operation input is entered in the operating button 22, i.e., in the second supply state, the resultant acting on the protrusion 33 remains unchanged.

When the operating button 21 is pressed, the operating button 21 is pressed against the slider 53 from the proximal-end side. Pressed toward the distal-end side by the operating button 21, the slider 53 is moved toward the distal-end side with respect to the movable pipe 31, compressing the spring 55 from its natural state. The spring 55 is compressed from its natural state when pressed toward the distal-end side by the operating button 21. The resilient force F2 (=k2·x2) from the spring 55 acts on the slider 43 toward the distal-end side. Therefore, the protrusion 33 is pressed toward the distal-end side by the spring 55 through the slider 43 and the spring 45.

When an operation input is entered in the operating button 21, i.e., in the first supply state, the protrusion 33 of the movable pipe 31 is pressed toward the distal-end side under the resilient force F1 from the spring 45 and pressed toward the distal-end side under the resilient force F2 from the spring 55. Therefore, the resultant that represents the sum of the resilient force F1 from the spring 45 and the resilient force F2 from the spring 55 acts on the movable pipe 31 toward the distal-end side. According to the present modification, therefore, when an operation input is entered in the operating button 21, the resultant of the resilient force F1 and the resilient force F2 acting on the protrusion 33 is larger than when an operation input is entered in the operating button 22. Consequently, in the first supply state, the resultant acting on the movable pipe 31 is larger than in the second supply state.

According to the present modification, therefore, in the first supply state for incising the treatment target, a larger gripping force is applied to the treatment target than in the second supply state for sealing the treatment target. Therefore, since the gripping force applied to the treatment target is variable depending on a treatment on the treatment target, a gripping force suitable for the treatment can be applied to the treatment target.

Other Embodiments

The arrangements according to the above embodiments or the like are applicable to an embodiment in which bipolar electrodes are included as the first electric element 27 and an ultrasonic transducer is included as the second electric element 28. In this case, a sealing device that applies only a high-frequency electric current to a treatment target should preferably apply a large gripping force to the treatment target. On the other hand, an incising device that applies both high-frequency current and ultrasonic vibrations to a treatment target is unable to apply a large gripping force for increased transmittability of the ultrasonic vibrations.

For example, in a case where bipolar electrodes and an ultrasonic transducer are included in the arrangement according to the first embodiment, when an operation input is entered in the operating button 21, i.e., in the first supply state, the treatment target is incised, and when an operation input is entered in the operating button 22, i.e., in the second supply state, the treatment target is sealed. In this case, in the second supply state for performing a treatment to seal the treatment target, a larger gripping force can be applied to the treatment target than in the first supply state for incising the treatment target.

For example, furthermore, in a case where bipolar electrodes and an ultrasonic transducer are included in the arrangement according to the second modification of the first embodiment, when an operation input is entered in the operating button 21, i.e., in the first supply state, the treatment target is sealed, and when an operation input is entered in the operating button 22, i.e., in the second supply state, the treatment target is incised. In this case, in the first supply state for performing a treatment to seal the treatment target, a larger gripping force can be applied to the treatment target than in the second supply state for incising the treatment target. As described hereinbefore, according to an embodiment in which high-frequency electric current and ultrasonic vibrations are used as treatment energy, a gripping force suitable for a selected treatment mode can be applied to the treatment target.

Common Arrangement of the Embodiments and the Like

A surgical instrument (1) includes a sheath (5) extending along a longitudinal axis (C) from a proximal end toward a distal end, a pair of grasps (13 and 14) disposed on a distal-end portion of the sheath (5), gripping a treatment target therebetween, a drive shaft (15) coupled to at least one of the pair of grasps (13 and 14) and movable along the longitudinal axis (C) with respect to the sheath (5) opening or closing the space between the pair of grasps (13 and 14), electric elements (27 and 28) applying treatment energy to the treatment target by being supplied with electric energy, a first operating device (21) supplying the electric energy to the electric elements (27 and 28) in a first supply state in response to an operation input entered therein, a first resilient member (45) applying a resilient force (F1) to the drive shaft (15), a slider (43) disposed movably with respect to the drive shaft (15) and changing a distance (x1) by which the first resilient member (45) is compressed by being moved with respect to the drive shaft (15), and a second resilient member (55) applying a resilient force (F2) to the drive shaft (15), the second resilient member (55) being disposed coaxially with and in line with the first resilient member (45) and compressible by a distance (x2) that changes depending on the operation input entered in the first operating device (21).

The disclosed technology is not limited to the above embodiments and various modifications may be made therein without departing from the scope of the invention when it is reduced to practice. The embodiments may be appropriately combined as much as possible, and the combinations offer combined advantages. Furthermore, the embodiments include inventions in various stages, and various inventions can be extracted by appropriately combining a plurality of components that are disclosed.

In sum, the disclosed technology is directed to a surgical instrument comprises a sheath having respective opposed proximal and distal ends extending along a longitudinal axis. A pair of grasps is disposed on the distal-end portion of the sheath gripping a treatment target therebetween. A drive shaft is configured to be coupled to at least one of the pair of grasps to open or to close the pair of grasps with respect to one another by being moved along the longitudinal axis with respect to the sheath. Electric elements are used to apply treatment energy to the treatment target using electric energy. A first operating device supplies the electric energy to the electric elements in a first supply state in response to an operation input entered therein. A first member produces a force to open or close the pair of grasps with respect to one another and applies the force to the drive shaft. A second member is disposed in line with the first member along the longitudinal axis. The second member applies a force to the drive shaft in response to the operation input entered in the first operating device.

The surgical instrument further comprises a second operating device supplies the electric energy to the electric elements in a second supply state different from the first supply state in response to an operation input entered therein. A resultant of one force acting from the first member on the drive shaft and another force acting from the second member on the drive shaft in the first supply state is different from the resultant of the one force acting from the first member on the drive shaft and the another force acting from the second member on the drive shaft in the second supply state. The resultant force acting on the drive shaft in the first supply state is smaller than the resultant force acting on the drive shaft when the operation input is entered in the second operating device. The electric elements include a heater transmitting heat to the electrodes disposed respectively in the pair of grasps. The electric energy supplied to the electrodes in the first supply state and the electric energy supplied to respective the electrodes and the heater in the second supply state. The electric elements include an ultrasonic transducer generating ultrasonic vibrations supplied with the electric energy and the electrodes disposed respectively in the pair of grasps.

The electric energy is supplied to the respective electrodes and the ultrasonic transducer in the first supply state and the electric energy being supplied to the electrodes in the second supply state. The resultant force acting on the drive shaft in the first supply state is larger than the resultant force acting on the drive shaft in the second supply state. The electric elements include a heater transmitting heat to the electrodes disposed in the respective pair of grasps. The electric energy is supplied to the respective electrodes and the heater in the first supply state and the electric energy is supplied to the electrodes in the second supply state. The electric elements include an ultrasonic transducer generating ultrasonic vibrations supplied with the electric energy and the electrodes disposed in the respective pair of grasps. The electric energy is supplied to the electrodes in the first supply state. The electric energy is supplied to the respective electrodes and the ultrasonic transducer in the second supply state. A direction of the force acting from the second member on the drive shaft is directed to an opposite side to a direction of the force acting from the first member on the drive shaft.

A direction of the force acting from the second member on the drive shaft is directed to a same side as a direction of the force acting from the first member on the drive shaft. The first member includes a first resilient member applying a first resilient force to the drive shaft and the second member includes a second resilient member applying a second resilient force to the drive shaft. The surgical instrument further comprises a slider changing a distance by which the first resilient member is compressed by being moved along the longitudinal axis with respect to the drive shaft. The respective first and second resilient members are disposed coaxially with the drive shaft. The operation input is entered in the first operating device when the distance by which the second resilient member is compressed is equal to or larger than a predetermined value.

Another aspect of the disclosed technology is directed to a treatment tool comprises a housing having respective first and second ends. A sheath is configured to be attached to the first end of the housing. The sheath having respective opposed proximal and distal ends extending along a longitudinal axis. An effector is mounted to the sheath. The end effector includes a pair of grasps disposed on the distal-end portion of the sheath gripping a treatment target therebetween. A power supply device is attached to the second of the housing via a cable. A drive shaft is configured to be coupled to at least one of the pair of grasps to open or to close the pair of grasps with respect to one another by being moved along the longitudinal axis with respect to the sheath. Electric elements is used to apply treatment energy to the treatment target using electric energy. A first operating device supplies the electric energy to the electric elements in a first supply state in response to an operation input entered therein. A first member produces a force to open or close the pair of grasps with respect to one another and applies the force to the drive shaft. A second member is disposed in line with the first member along the longitudinal axis. The second member applies a force to the drive shaft in response to the operation input entered in the first operating device. The treatment tool is a surgical instrument and the treatment target is a biological tissue.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future. The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A surgical instrument comprising:
   a sheath having respective opposed proximal and distal ends extending along a longitudinal axis;
   a pair of grasps disposed on a distal-end portion of the sheath, the pair of grasps being configured to grip a treatment target therebetween;
   a drive shaft coupled to at least one of the pair of grasps and configured to open or to close the pair of grasps relative to one another by being moved along the longitudinal axis relative to the sheath;
   electric elements configured to apply treatment energy to the treatment target using electric energy;
   a first button configured to receive an operation input;
   a power supply device configured to supply the electric energy to the electric elements in a first supply state in response to the operation input entered in the first button;
   a first member configured to produce a force to open or close the pair of grasps relative to one another and to apply the force to the drive shaft; and
   a second member having a first end and a second end, and being configured to apply a force to the drive shaft in response to the operation input entered in the first button,
   wherein:
   in the first supply state, the second end of the second member contacts the first button, and
   in a second supply state in which an operation input has not been entered in the first button, the second end of the second member is spaced apart from the first button.

2. The surgical instrument of claim 1, further comprising:
   a second button configured to receive an operation input,
   wherein the power supply device is further configured to supply the electric energy to the electric elements in the second supply state different from the first supply state in response to the operation input entered in the second button.

3. The surgical instrument of claim 2, wherein
   a resultant force acting on the drive shaft in the first supply state is different from the resultant force acting on the drive shaft in the second supply state, the resultant force being the resultant of one force acting from the first member on the drive shaft and another force acting from the second member on the drive shaft.

4. The surgical instrument of claim 3, wherein
   the resultant force acting on the drive shaft in the first supply state is smaller than the resultant force acting on the drive shaft when the operation input is entered in the second button.

5. The surgical instrument of claim 4, wherein
   the electric elements include:
      electrodes disposed respectively in the pair of grasps; and
      a heater configured to transmit heat to the electrodes,
   the power supply device is configured to supply the electric energy to the electrodes in the first supply state, and
   the power supply device is configured to supply the electric energy to the respective electrodes and the heater in the second supply state.

6. The surgical instrument of claim 4, wherein
   the electric elements include:
      an ultrasonic transducer configured to generate ultrasonic vibrations; and electrodes disposed respectively in the pair of grasps;
the power supply device is configured to supply the electric energy to the respective electrodes and the ultrasonic transducer in the first supply state; and
the power supply device is configured to supply the electric energy to the electrodes in the second supply state.

7. The surgical instrument of claim 3, wherein
the resultant force acting on the drive shaft in the first supply state is larger than the resultant force acting on the drive shaft in the second supply state.

8. The surgical instrument of claim 7, wherein
the electric elements include:
electrodes disposed in the respective pair of grasps; and
a heater configured to transmit heat to the electrodes,
the power supply device is configured to supply the electric energy to the respective electrodes and the heater in the first supply state; and
the power supply device is configured to supply the electric energy to the electrodes in the second supply state.

9. The surgical instrument of claim 7, wherein
the electric elements include:
an ultrasonic transducer configured to generate ultrasonic vibrations; and
electrodes disposed in the respective pair of grasps;
the power supply device is configured to supply the electric energy to the electrodes in the first supply state; and
the power supply device is configured to supply the electric energy to the respective electrodes and the ultrasonic transducer in the second supply state.

10. The surgical instrument of claim 1, wherein
a direction of the force acting from the second member on the drive shaft is opposite to a direction of the force acting from the first member on the drive shaft.

11. The surgical instrument of claim 1, wherein
a direction of the force acting from the second member on the drive shaft is the same as a direction of the force acting from the first member on the drive shaft.

12. The surgical instrument of claim 1, wherein:
the first member comprises a first resilient member configured to apply a first resilient force to the drive shaft,
the second member comprises a second resilient member configured to apply a second resilient force to the drive shaft, and
the surgical instrument further comprises a slider configured to change a distance by which the first resilient member is compressed by being moved along the longitudinal axis with respect to the drive shaft.

13. The surgical instrument of claim 12, wherein
the respective first and second resilient members are disposed coaxially with the drive shaft.

14. The surgical instrument of claim 12, wherein
the operation input is entered in the first button when the distance by which the second resilient member is compressed is equal to or larger than a predetermined value.

15. The surgical instrument of claim 1, wherein the second member is disposed end-to-end with the first member along the longitudinal axis.

16. A treatment tool comprising:
a housing having respective first and second ends;
a sheath configured to be attached to the first end of the housing, the sheath having respective opposed proximal and distal ends extending along a longitudinal axis;
an end effector mounted to a distal-end portion of the sheath, the end effector including a pair of grasps configured to grip a treatment target therebetween;
a power supply device attached to the second end of the housing via a cable;
a drive shaft coupled to at least one of the pair of grasps and configured to open or to close the pair of grasps relative to one another by being moved along the longitudinal axis relative to the sheath;
electric elements configured to apply treatment energy to the treatment target using electric energy;
a first button configured to receive an operation input;
a power supply device configured to supply the electric energy to the electric elements in a first supply state in response to the operation input entered in the first button;
a first member configured to produce a force to open or close the pair of grasps relative to one another and to apply the force to the drive shaft; and
a second member having a first end and a second end, and being configured to apply a force to the drive shaft in response to the operation input entered in the first button,
wherein:
in the first supply state, the second end of the second member contacts the first button, and
in a second supply state in which an operation input has not been entered in the first button, the second end of the second member is spaced apart from the first button.

17. The treatment tool of claim 16, which is a surgical instrument.

18. The treatment tool of claim 16, wherein the treatment target is a biological tissue.

19. The treatment tool of claim 16, wherein the second member is disposed end-to-end with the first member along the longitudinal axis.

20. A surgical instrument comprising:
a sheath having respective opposed proximal and distal ends extending along a longitudinal axis;
a pair of grasps disposed on a distal-end portion of the sheath, the pair of grasps being configured to grip a treatment target therebetween;
a drive shaft coupled to at least one of the pair of grasps and configured to open or to close the pair of grasps relative to one another by being moved along the longitudinal axis relative to the sheath;
electric elements configured to apply treatment energy to the treatment target using electric energy;
a first button configured to receive an operation input;
a power supply device configured to supply the electric energy to the electric elements in a first supply state in response to an operation input entered in the first button;
a first member configured to produce a force to open or close the pair of grasps relative to one another and to apply the force to the drive shaft; and
a second member configured to apply a force to the drive shaft in response to the operation input entered in the first button, wherein a resultant force acting on the drive shaft in the first supply state is different from the resultant force acting on the drive shaft in a second supply state in which an operation input has not been entered in the first button, the resultant force being the resultant of one force acting from the first member on the drive shaft and another force acting from the second member on the drive shaft.

* * * * *